US010800820B2

(12) United States Patent
Kottwitz et al.

(10) Patent No.: US 10,800,820 B2
(45) Date of Patent: Oct. 13, 2020

(54) PREPARATION METHODS FOR A NOVEL GENERATION OF BIOLOGICAL SAFE KLH PRODUCTS USED FOR CANCER TREATMENT, FOR THE DEVELOPMENT OF CONJUGATED THERAPEUTIC VACCINES AND AS CHALLENGING AGENTS

(71) Applicant: Biosyn Arzneimittel GmbH, Fellbach (DE)

(72) Inventors: Ortwin Kottwitz, Korntal-Münchingen (DE); Thomas Stiefel, Stuttgart (DE); Shammana N. Muddukrishna, Carlsbad, CA (US)

(73) Assignee: Biosyn Arzneimittel GmbH, Fellbach (DE)

( * ) Notice: Subject to any disclaimer, the term of this patent is extended or adjusted under 35 U.S.C. 154(b) by 0 days.

(21) Appl. No.: 15/318,286

(22) PCT Filed: Jun. 12, 2014

(86) PCT No.: PCT/EP2014/062278
§ 371 (c)(1),
(2) Date: Dec. 12, 2016

(87) PCT Pub. No.: WO2015/188869
PCT Pub. Date: Dec. 17, 2015

(65) Prior Publication Data
US 2017/0121376 A1    May 4, 2017

(51) Int. Cl.
| | |
|---|---|
| *C07K 14/435* | (2006.01) |
| *B01D 15/36* | (2006.01) |
| *C07K 1/18* | (2006.01) |
| *B01J 41/07* | (2017.01) |
| *B01J 41/20* | (2006.01) |
| *A61K 39/385* | (2006.01) |
| *C12N 7/00* | (2006.01) |
| *A61K 39/00* | (2006.01) |

(52) U.S. Cl.
CPC ...... *C07K 14/43504* (2013.01); *A61K 39/385* (2013.01); *B01D 15/363* (2013.01); *B01J 41/07* (2017.01); *B01J 41/20* (2013.01); *C07K 1/18* (2013.01); *C12N 7/00* (2013.01); *A61K 2039/6081* (2013.01)

(58) Field of Classification Search
CPC ...... C07K 14/43504; C07K 1/18; B01J 41/07; B01J 41/20; A61K 39/385; A61K 2039/6081; C12N 7/00; B01D 15/363
See application file for complete search history.

(56) References Cited

U.S. PATENT DOCUMENTS

2002/0151688 A1  10/2002  Ristol Debart et al.
2007/0142590 A1   6/2007  Rasmussen et al.

FOREIGN PATENT DOCUMENTS

| | | |
|---|---|---|
| EP | 0621039 A1 | 10/1994 |
| EP | 1457497 A1 | 9/2004 |
| RU | 2040261 C1 | 7/1995 |
| WO | WO 2001/25285 A1 | 4/2001 |
| WO | WO 02/102844 A1 | 12/2002 |
| WO | WO 2004/085467 A1 | 10/2004 |
| WO | WO 2005/014647 A1 | 2/2005 |
| WO | WO 2005/073252 A1 | 8/2005 |

OTHER PUBLICATIONS

Ritchie, C. Protein Purification. Materials and Methods 2012; 2:134.*
Wikipedia entry for "Colloid" retrieved Aug. 19, 2019 from https://en.wikipedia.org/wiki/Colloid.*
Burnouf & Radosevich, "Nanofiltration of plasma-derived biopharmaceutical products," *Haemophilia* 9: 24-37 (2003).
European Patent Office, International Search Report in International Application No. PCT/EP2014/062276 (dated Nov. 21, 2014).
Adluri et al., "Immunogenicity of synthetic TF-KLH (keyhole limpet hemocyanin) and sTn-KLH conjugates in colorectal carcinoma patients," *Cancer Immunol., Immunother.*, 41(3): 185-192 (1995) (Abstract only).
"Application Note: POROS® HQ 50 Chromatography Resin," *Applied Biosystems by Life Technologies* (2012).
Eon-Duval & Burke, "Purification of pharmaceutical-grade plasmid DNA by anion exchange chromatography in an RNase-free process," *J. Chromatography B. Analyt. Technol. Biomed. Life Sci.*, 804(2): 327-335 (2004) (Abstract Only).
Parra & Gebski, "Benefits of a Revised Approach to Anion Exchange Flow-Through Polish Chromatography," *BioPharm International*, 24(4): s1-s5 (2011).
"POROS® 20 Micron HQ and PI Perfusion Chromatography® Bulk Media for Anion Exchange Chromatography Operating Instructions," *Applied Biosystems* (2002).
"POROS® 50 Q Perfusion Chromatography® Bulk Media for Anion Exchange Chromatography Operating Instructions," *Applied Biosystems* (2001).
Dolashka-Angelova et al., *Biochimica et Biophysica Acta*, 1646: 77-85 (2003).
Harris et al., *Micron*, 28(1): 43-56 (1997).
Harris et al., *Micron*, 30(6): 597-623 (1999).
Ioannes et al., *The Journal of Biological Chemistry*, 279(25): 26134-26142 (2004).
McFadden et al., *The American Journal of Surgery*, 186: 552-555 (2003).
Swerdlow et al., *Comp. Biochem. Physiol.*, 113B(3): 537-548 (1996).
European Patent Office, International Search Report in International Application No. PCT/EP2014/062278 (dated Dec. 3, 2014).

(Continued)

*Primary Examiner* — Gregory S Emch
(74) *Attorney, Agent, or Firm* — Leydig, Voit & Mayer, Ltd.

(57) ABSTRACT

The present invention relates to the provision of a biologically safe hemolymph sera, preferably hemocyanin, more preferably KLH (keyhole limpet hemocyanin). The hemocyanin is purified using anion exchange chromatography.

18 Claims, No Drawings

(56) References Cited

OTHER PUBLICATIONS

Campello et al., "Role of the tertiary structure in the diphenol oxidase activity of *Octopus vulgaris* hemocyanin", *Archives of Biochemistry and Biophysics*, 471: 159-167 (2008).
Idakieva et al., "Rapana thomasiana hemocyanin (RtH): dissociation and reassociation behavior of two isoforms, RtH1 and RtH2", *Micron*, 33: 7-14 (2002).
Milbrandt et al., "Development of a 20N Virus Filtration Process for Keyhole Limpet Hemocyanin (KLH)—A High Molecular Weight Protein," Poster presented at PepTalk Protein Science Week, Jan. 18-22, 2016, San Diego, CA.

\* cited by examiner

PREPARATION METHODS FOR A NOVEL GENERATION OF BIOLOGICAL SAFE KLH PRODUCTS USED FOR CANCER TREATMENT, FOR THE DEVELOPMENT OF CONJUGATED THERAPEUTIC VACCINES AND AS CHALLENGING AGENTS

CROSS REFERENCE TO RELATED APPLICATIONS

This patent application is the U.S. national phase of International Patent Application No. PCT/EP2014/062278, filed Jun. 12, 2014, the disclosure of which is incorporated herein by reference in its entirety for all purposes.

BACKGROUND OF THE INVENTION

The present invention relates to the provision of a biologically safe hemolymph sera, preferably hemocyanin, more preferably KLH (keyhole limpet hemocyanin).

Hemocyanin is a blue copper protein which occurs in a freely dissolved form in the blood of numerous molluscs and arthropods and transports oxygen. Of the molluscs, the cephalopods, chitons, most gastropods and some bivalves contain hemocyanin. Among the arthropods, hemocyanin is typical of arachnids, xiphosurans, malacostracan crustaceans and Scutigera. Numerous species of insects contain proteins which are derived from hemocyanin. Hemocyanins are present in the extracellular medium and float in the hemolymph.

While arthropod hemocyanin has a maximum diameter of 25 nm under an electron microscope and a subunit has a molecular weight of 75,000 Dalton (Da), mollusc cyanins are much larger. Thus e.g. the hemocyanin of *Megathura* has a diameter of 35 nm and is composed of 2 subunits. Each subunit has a molecular weight of approx. 400,000 Da and is divided into eight oxygen-binding domains, each of which has a molecular weight of approx. 50,000. The domains differ immunologically.

The hemocyanin of gastropods visible under an electron microscope has a molecular weight of approx. 8 million Da and is a didecamer. In contrast to this, the hemocyanin of cephalopods is arranged as an isolated decamer, which also differs significantly from the hemocyanin of gastropods in the quaternary structure.

Traditionally, hemocyanin was obtained from hemolymph from the *Megathura crenulata*. More recently, the market for gastropod hemocyanins has expanded to include hemocyanin from *Haliotis tuberculate* and *Concholepus concholepus*. The hemolymph from other gastropod molluscs is also under investigation for useful properties.

The hemocyanin of the Californian keyhole limpet *Megathura crenulata* is of particular immunological interest. The hemocyanin is therefore also called keyhole limpet hemocyanin (KLH). Hemocyanins are very potent antigens. Immunization of a vertebrate leads to a non-specific activation of the immune system which to date is not very well understood. By the general activation of the immune system, it is then possible also to achieve an immune reaction to other foreign structures which have previously been tolerated. KLH is used above all as a hapten carrier in order thus to achieve the formation of antibodies against the hapten.

In addition to *Megathura crenulata*, the abalone *Haliotis tuberculate* also belongs to the Archaegastropoda group, which is relatively old in respect of evolution. It is known that *Haliotis* also produces hemocyanin.

Native KLH is found in the hemolymph (pH 6.0-8.0) in colloidal solution as a didecamer (molecular weight: around 8 million Da) and as multidecamers (molecular weight: 12 to about 32 million Da). The quantitative distribution of these aggregates varies. The didecamers and multidecamers of KLH are composed of 2 types of subunits with an average molecular weight of around 400,000 Da. The two different types of subunits as well as the two different aggregation types are due to the fact that native KLH is a mixture of two different types KLH 1 and KLH 2.

KLH is a mixture of two different hemocyanins, which are called KLH1 and KLH2. The subunit of KLH1 is a 390 kDa polypeptide which consists of eight globular domains called 1 a to 1 h according to their sequence in the subunit. On the other hand, KLH2 has a molecular weight of 360 kDa and according to the most recent data also contains 8 domains, called 2 a to 2 h. In vivo every type of subunit forms homo-oligomers, while no hetero-oligomers have been observed.

Hemocyanins may be obtained in farms from test animals. Methods described for collection of hemolymph involve inserting a needle into a muscle of the foot to penetrate the pedal blood sinus (Harris et al., "Keyhole Limpet Haemocyanin: Negative Staining in the Presence of Trehalose," Micron, 26 (1): 25-33 (1995). Semi-automated systems were established allowing the collection of high amounts of hemolymph without killing the animals. The manufacturing procedures allow extracting commercial quantities of hemocyanin from animals grown in a controlled environment (WO 02/085389, US2002/192633).

There are a variety of well-known methods for purifying hemocyanins from crude hemolymph, which is the biological source of hemocyanins. These methods include differential centrifugation, gel-permeation chromatography, and ion-exchange chromatography (U.S. Pat. No. 5,407,912). Purified hemocyanins are commercially available in many forms.

The incorporation of hemocyanins into promising new therapeutic products (see e.g., Jurincic-Winkler et al., "Antibody Response to Keyhole Limpet Hemocyanin (KLH) Treatment in Patients with Superficial Bladder Carcinoma," Anticancer Res., 16 (4A): 2105-10 (1996); and Biomira, Inc. Company Press Release, Biomira.com, 2001) has resulted in the need for a sustainable supply of commercial quantities of hemocyanin produced under conditions that meet the health and safety standards imposed by the United States Food and Drug Administration and other regulatory agencies.

BRIEF SUMMARY OF THE INVENTION

Due to their native origin, hemocyanins such as KLH, suffer from the risk of bio-contamination by pathogens such as pathogenic blood ingredients, such as toxins, bacteria, including endotoxins produced thereby, as well as viruses.

It is therefore an object of the present invention to provide means and ways in order to minimize the bio-burden by pathogens in native hemocyanin. This includes the further object of providing a process with which safe and highly pure hemocyanin can be prepared.

The present inventors have identified that blood and hemolymph taken from molluscs immediately harvested from the sea may be contaminated by viruses bacteria, toxins or endotoxins. There is, thus, a need for reducing the contamination in the molluscs and the blood or hemolymph obtained therefrom.

Conventionally, for the removal of viruses there are different processes that can be used: virus inactivation, e.g.

the treatment of the protein using the detergent/solvent method, ionised radiation, thermal treatment (ca. 60° C.) and the incubation at pH values<3. These processes cannot be used in the treatment of hemocyanins such as KLH because they lead to a denaturisation of the protein. Due to the high molecular structure of KLH it is extremely sensitive to these inactivating methods. Also other approaches such as virus nanofiltration that have been developed in the past few years cannot be used. These filters do not allow a significant virus removal rate due to the small size difference between viral contamination and the target protein. Gelfiltration that works by separating the molecular weight is also not suitable for the removal of viral contaminants because the size of the viruses do not vary significantly from those of hemocyanins.

Thus, there is a need to provide new means for reducing virus load in hemocyanins and for the separation of viruses from hemocyanins.

It is further an object underlying the present invention to provide therapeutically valuable amounts of hemocyanins, e.g. KLH, or subunits thereof, such as immunocyanin. These amounts need to be provided in a purified and isolated manner. Accordingly, means and methods for isolating and purifying hemocyanins and subunits thereof (e.g. KLH or immunocyanin) are needed.

The present inventors have tested several purification methods. Among these, ultracentrifugation is limited in handling due to limited quantities of hemocyanin which be provided. It is further time consuming and accordingly expensive. There is a need for a cheaper isolation and purification approach allowing the production of hemocyanin, such as KLH, or hemocyanin subunits, such as immunocyanin. Gelfiltration chromatography was not successful. Hydrophobic interaction chromatography was selected for further evaluation but turned out to be unsuitable for the intended isolation and purification.

Ion exchange chromatography relies on charge-charge interactions between the proteins in the sample and the charges immobilized on the concerned resin. Cation exchange chromatography employs positively charged molecules attached to a negatively charged solid support.

After conducting a laborious research program, the present inventors found that anion exchange chromatography, which employs negatively charged molecules attached to a positively charged solid support, turned out to be suitable for the intended isolation and purification. More preferably, a specific anion exchange column is provided comprising a specific matrix material (see embodiment 1). In another preferred embodiment, a specific method for isolating and/or purifying hemocyanin, e.g. KLH, and/or its subunits, e.g. immunocyanin, is provided (see embodiments 2-7).

Preferred embodiments of the invention are:
1. Anion exchange chromatography column comprising a matrix material with a particle size of more than 30 µm, preferably more than 40 µm, and a pore size of between 3 000 and 8 000 Å (Angstroem), preferably 6 000-8 000 Angstroem.
2. A method of isolating and/or purifying hemocyanin or immunocyanin comprising the steps of:
   a) providing a hemocyanin formulation derived from a marine mollusc;
   b) reducing the conductivity of the formulation provided in a) to a value of between 10 mS/cm and 30 mS/cm by adding a dilution buffer;
   c) adding the diluted hemocyanin formulation obtained in step b) to an anion exchange chromatography column;
   d) rinsing the column with a buffer to purify the hemocyanin, preferably to remove salts, and other proteins; and
   e) eluting the hemocyanin or immunocyanin from the column by adding a second buffer.
3. The method according to embodiment 2 wherein the buffer for purifying is a buffer in the pH between 7 and 8.
4. The method of any of embodiments 2-3, wherein hemocyanin is eluted, wherein a buffer of a pH between 7 and 8 is used which includes $Ca^{++}$ and $Mg^{++}$ ions.
5. The method according to any of embodiments 2-3, wherein immunocyanin is eluted, wherein a buffer is employed of a pH between 9 and 10 which is free from $Ca^{++}$ and $Mg^{++}$ ions.
6. The method of any of embodiments 2-5, wherein the matrix material is an anion exchange matrix including particles of a particle size of more than 30 µm, preferably more than 40 µm, more preferably 50 µm+/−5 µm.
7. The method of any of embodiments 2-6, wherein the anion exchange matrix includes pores of a pore size between 3 000 and 8 000 Angstroem, preferably 6 000-8 000 Angstroem.
8. Use of the anion exchange chromatography column of embodiment 1 for purifying hemocyanin or its subunits.

In order to optimize the binding of charged hemocyanin or its subunits (KLH or immunocyanin) to the anion exchange column, the protein formulation (solution or suspension) put onto the column needed to be lowered in its conductivity. The selection of anion exchange chromatography among other isolation and purification methods as well as the selection of a matrix material are described in Example 9.

One task the present inventors were faced with was the identification of a most preferred matrix material. Due to the size of the hemocyanin and its subunits, a matrix material with small particles turned out not to be useful. A particle size of at least 30 µm diameter turned out to be helpful. In a more preferred embodiment, the particle size is at least 45 µm diameter, even more preferred are 50 µm+/−5 µm diameter. The capacity of the matrix material depended on the size of the "through-pores" or "pores". A porous material with pores of at least 3,000 Angstroem was found to be most preferred. The pore size may be between 3,000-8,000 Angstroem or preferably between 6,000-8,000 Angstroem. The material may be a conventional material useful for ion exchange chromatography in the pH range of between 6-10, preferably in the range between 7-9. Using anion exchange chromatography with such a matrix material achieved highest degrees of purity of more than 90%, preferably 95% or more preferably 99%. More than 15 mg/ml, preferably more than 17 mg/ml, more preferably more than 23 mg/ml matrix material of KLH are bound to the column.

Hemocyanin formulations such as hemolymph sera or subunits thereof, such as immunocyanin, could not be applied directly to the column. The present inventors identified that typical hemocyanin formulations, and as hemolymph sera derived from marine molluscs contain, apart from hemocyanin and other serum components, high levels of sodium chloride and other minerals. This leads to a very high conductivity in a range of approximately 50 mS/cm. Under these conditions, the protein formulation (e.g. the hemolymph serum) cannot be bound to the ion exchange column. In order to achieve a quantitative binding of the protein formulation, a dilution in buffer was necessary. The buffer is a buffer in the pH range between 6 and 8, preferably between 7 and 7.5. The buffer preferably includes $Ca^{++}$ and $Mg^{++}$ ions. The buffer needs to be suitable to dilute the mineral and salt components. In particular, the buffer needs to be suitable to lower the conductivity. To achieve a quantitative binding of the hemocyanin formulation (or the protein formulation in more general terms), the conductivity needs to be lowered below 25 mS/cm, preferably below 20 mS/cm. A preferred range is between 10 and 20 mS/cm.

A preferred medium is Poros® 50 HQ.

The linear flow rate of the sample may be between 10 ml/min and 100 ml/min, preferably between 30 and 70 ml/min, most preferably 50 ml/min.

After reducing conductivity as described above, the protein formulation (the hemocyanin formulation) is loaded onto the anion exchange column.

Under neutral pH conditions (pH between 6 and 8, preferably between 7 and 7.5), the hemocyanin binds to the anion exchange column. Elution of other proteins, salts, minerals and/or other molecules is effected. Preferably, a buffer as used for diluting and reducing conductivity is employed.

After the rinsing step, a purified protein from a hemocyanin formulation is bound to the anion exchange column.

If it is intended to elute the hemocyanin, such as KLH, without dissociation, the hemocyanin is eluted from the column using an elution buffer in the neutral range (pH between 6 and 8, preferably between 7 and 7.5). The elution buffer is increased in its ionic strength as compared to the rinsing buffer. In a preferred embodiment, the elution buffer comprises $Ca^{++}$ and $Mg^{++}$ ions, more preferably in a concentration between 0.01 M and 0.1 M, even more preferably between 0.05 and 0.01 M, each. In a more preferred embodiment, the buffer alternatively or additionally comprises TRIS/HCL, preferably in a concentration between 0.1 and 1 M.

The difference between the rinsing and the elution buffer may be the salt concentration.

Typically for elution, an elution gradient is applied employing 0.01 up to 1 M sodium chloride, more preferably between 0.05 and 0.7 M, most preferably between 0.075 and 0.575 M sodium chloride.

If it is intended to dissociate the hemocyanin into its subunits, e.g. KLH subunits or immunocyanin, before eluting, an alkaline buffer is added (pH between 8 and 10, preferably between 9 and 10). The dissociation buffer may be a dissociation buffer as described elsewhere in the specification. Preferably, the dissociation buffer contains glycine and NaOH. It may also contain NaCl and/or EDTA. Under these conditions, the hemocyanin dissociates into its subunits. The dissociation buffer is free from $Ca^{++}$ and $Mg^{++}$ and is preferably used in an amount and concentration to remove $Ca^{++}$ and $Mg^{++}$ ions from the column. The dissociation buffer can be used for elution as well. Again, an elution gradient with increased salt concentrations is employed for eluting. In the preferred embodiment, the elution gradient is as described for hemocyanin as above.

To solve other problems, the present invention provides the methods and compounds and compositions set forth below:

In a first aspect the present invention provides a method for the preparation of hemolymph sera from a mollusc is provided, the method comprising a step of puncturing the pedal blood sinus of the mollusc under cold narcosis.

Preferably, the mollusc is *Megathura crenulata*. Other molluscs are e.g. *Haliotis tuberculata* (European Abalone), *Haliotis rubra* (Australian Abalone)

In a preferred embodiment, during puncturing the mollusc is kept under specific quarantine conditions, wherein the molluscs after being obtained from their natural sources are kept in a quarantine aquarium system under conditions, wherein no organic feed is supplied and/or the water in the aquarium system is purified by removing biological contaminants. The removing of biological contaminants may include bio-filtration, protein skimming, etc.

The blood obtained upon puncturing may further be sterilized, preferably by using 0.2 µm membrane filtration.

In a second aspect the present invention provides a method of isolating native hemocyanin comprising providing hemolymph sera, such as those obtained in the method of the first aspect, and isolating the hemocyanin, such as KLH, from hemolymph sera, preferably by employing direct chromatography.

In a preferred embodiment, the direct chromatography is an ion exchange chromatography.

The method may further include a step of dissociating the hemocyanin into subunits of the hemocyanin oligomer. Optionally a step of purifying the hemocyanin subunits is performed as well. Optionally, a step of re-associating the subunits into the oligomeric form of the hemocyanin is performed.

In a preferred embodiment the purification of hemocyanin subunits is performed including a step of nanofiltration in order to remove potential biological contamination.

Preferably, the re-association step takes place comprising a diafiltration step or a dialysis step. The re-associated hemocyanin may be finally purified by gel filtration.

Preferably, the hemocyanin is admixed stabilizing puffer system for long-term storage.

In this aspect, also provided is a method of producing synthetic hemocyanin such as synthetic KLH, comprising a step of dissociating the hemocyanin, e.g. native KLH, to obtain subunits, nanofiltrating the subunits so obtained using filters removing viruses, preferably nanofilters with a pore size between 15 and 35 nm, more preferably between 20 and 25 nm and reassociating the subunits obtained after nanofiltering to obtain the synthetic hemocyanin, preferably the synthetic KLH.

In a preferred embodiment, the subunits are immunocyanin. More preferably, the subunits are smaller than 800,000, 500,000, 400,000, 350,000 or 300,000 Dalton, respectively. Most preferably, the subunits are between 300,000 and 500,000 Dalton.

In this aspect of the invention, the dissociation of hemocyanin into subunits is effected by applying a pH of between 8 and 10, preferably 9 and 10. Preferably, the dissociation takes place at an alkaline pH between 8 and 10, preferably 9 and 10 under removal of the bivalent cations calcium ($Ca^{++}$) and the magnesium ($Mg^{++}$). Removal of $Ca^{++}$ and $Mg^{++}$ may be effected by adding a chelat forming agent, e.g. EDTA. Under these conditions, native KLH dissociates into subunits. It has been found that the dissociation is reversible, i.e. the subunits can be reassociated by re-establishing a neutral pH value (between 6 and 9, preferably between 7 and 8) to a heterogeneous mixture of didecamers and multidecamers, preferably if $Ca^{++}$ and $Mg^{++}$ ions are added. A most preferred embodiment for dissociating hemocyanin such as native KLH, is as follows: The hemocyanin is stabilized in a stabilization buffer at a neutral pH including $Ca^{++}$ and $Mg^{++}$ ions, preferably a buffer including TRIS/HCL at a pH between 7 and 8. In this buffer, the hemocyanin is still in its native form without denaturating. An alkaline buffer is added which is in the range between 8 and 10, preferably 9 and 10. Most preferably, the temperature is below 10° C., most preferably below 5° C., especially between 2 and 8° C. Preferred alkaline buffers comprise glycine and NaOH. Other preferred buffers comprise TRIS/

HCl buffer pH 8.9, TRIS/HCl buffer pH 8.9 plus EDTA, Sodium phosphate buffer pH 8.0, Ammonium carbonate buffer pH 8.0, Sodium bicarbonate buffer pH 10.1, Sodium bicarbonate buffer pH 9.5, NaCl and/or EDTA may be added to the buffers. Typical buffer concentrations are 1-100 mM, preferably 2-50 mM, more preferably 10-20 mM. If EDTA is added, it is used in a concentration of 1/10 to 1/2 compared to the buffer concentration. Same concentrations as for EDTA are contemplated for NaCl, if added. The buffer may include EDTA and/or NaCl.

The so-obtained solution of subunits (or immunocyanin solution) is kept at the alkaline pH (between 8 and 10, preferably 9 and 10) and can be stored for more than one month, more than two months, most preferably more than three months, at a temperature below 10° C., more preferably between 2 and 8° C.

The subunits, e.g. immunocyanin, may be freed from a viral contamination. Nanofiltration was previously shown to effectively remove various viruses from protein solutions. However, the present inventors found that due to the enormous size and aggregation behaviour of KLH isomers, nanofiltration cannot be applied for KLH in its native form. The shift of the molecular weight of native KLH from more than 8 million Daltons to a molecular weight of less than 500,000 Daltons, typically to a uniform molecular weight of approximately 400,000 Daltons of the KLH subunits (immunocyanin), however, created the basis for the virus removal realized by the present inventors. Nanofiltrations can be made with commercially available nanofilters. Typically, these filters have a pore size of 15-35 nm, more preferably between 20-25 nm. Such filters are commercially available as filter capsules, for example Planova filter capsules. In one embodiment, such nanofilters are a single use unit. The nanofilters may utilize a low protein binding hollow-fibre microporous membrane constructed of naturally hydrophilic cuprammonium regenerated cellulose with a narrow pore distribution. A wide range of effective surface areas may be applied between 0.001 $m^2$ up to 4 $m^2$, preferably between 0.01 $m^2$ and 0.3 $m^2$.

The present inventors found that applying nanofiltration to hemocyanin subunits (immunocyanin) under typical conditions of commercial nanofilters was not very effective. Typically, proteins are nanofiltered by employing a protein suspension of solution and pumping the protein suspension of solution with a constant flow rate between 0.01 and 10 ml/minute, more preferably between 0.1 and 1 ml/minute into the filter so that the nanofilter surface is perpendicular to the flow direction. Such an approach is effective in virus removal. Unfortunately, due to the high molecular weight of KLH subunits (immunocyanin), the virus filters retain not only virus, but also high amounts of protein. The classical virus filtration with a flow perpendicular to the filter surface is also known as "dead-end filtration". The present inventors found that dead-end filtration is not preferred for virus removal in immunocyanin, or hemocyanin subunits. Hemocyanin, even after dissociation, cannot be nanofiltrated without a severe loss of protein. Example 2 compares "dead-end filtration" with the preferred mode of filtration of the present invention described herein below. Dead-end filtration leads to a loss of protein of more than 40%, more than 60% or even more than 80%.

Accordingly, there was a need for the provision of an improved and modified virus filtration approach. The present inventors found that the same nanofilters as described above need to be handled in a new and modified manner: The protein suspension or solution needs to be pumped with a flow parallel to the membrane surface. The flow rate may be between 0.01 and 100 ml/minute, preferable between 0.1 and 100 ml/minute, more preferably between 1 and 70 ml/minute. The pressure applied to the protein solution or suspension is lower than 0.1 MPa, preferably lower than 10 kPa. The protein solution or suspension is pumped or flow over the membrane surface, preferably in a repeated manner, more preferably, under the addition of more protein solution or suspension containing hemocyanin subunits so that a cycle including a raw material flow is established. The nanofiltration takes place preferably in an alkaline buffer, most preferably in the alkaline buffer used for dissociation. The starting material flown over the filter is preferably in a concentration range between 0.1 and 10 mg/ml, more preferably between 0.1 and 1 mg/ml, most preferably between 0.3 and 7 mg/ml. The protein yield after filtration is more than 80%, more preferably more than 90%, more preferably more than 93%.

The present inventors have established that with this nanofiltration approach, herein denominated "Cross-flow" filtration with flow direction parallel to the membrane surface of the nanofilter, almost quantitative protein purification is possible. Accordingly, the filtration is suitable for production of commercially relevant hemocyanin subunits or immunocyanin.

The present inventors also established that the virus load can be sufficiently reduced. With the methods of the present invention, preferably with cross-flow filtration, at least 99.9% of viruses are removed from the protein material. The so-called log reduction factor is a measure for the virus removal. The log reduction factor (LRF) is the amount of virus removed from the initial protein solution formulation, i.e. protein or protein suspension, expressed on a logarithmic scale (dec log scale). An LRF of 1 means that 90% of viruses are removed, 10% are retained. An LRF of 2 means 99% of viruses are removed, 1% is retained. An LRF of 3 means 99.9% of viruses are removed, 0.01% are retained. With the cross-flow filtration of the present invention, at least an LRF of 2 or more is obtained, more preferably an LRF of 3 or more is obtained. More preferably, an LRF of 4 or more is obtained.

The proof of concept is shown in Example 3 (feasibility study for cross-flow filtration). In this experiment, a 20 nm Planova filter with a filter surface of 0.12 $m^2$ was employed. The flow rate was 50 ml/minute. A total virus load of 10,620 (0.5% of the protein composition) was added. The virus employed for test purposes was PPV, one of the smallest viruses (diameter of 20 nm). A protein yield of more than 97% was achieved (4,662.4 g of purified protein compared 4,814.9 g pre-filtrate). LRF was 3.14+/−0.32.

The obtained filtrate may be used for therapeutic purposes (immunocyanin preparations). Accordingly, a method of producing immunocyanin comprising the steps of dissociating native hemocyanin to obtain subunits and nanofiltering the subunits so-obtained through a filter with a pore size between 15 and 35 nm is provided by the present invention. Preferably, the filtration is a cross-flow filtration. More preferably, the amount of an obtained protein is more than 60%, more than 70%, preferably more than 80%, more preferably more than 90%, most preferably more than 93% of immunocyanin or hemocyanin subunits.

In another embodiment, the immunocyanin or hemocyanin subunits are reassociated after the nanofiltering to obtain a "synthetic" hemocyanin, preferably "synthetic" KLH. The reassociation is effected by re-establishing a neutral pH value. The protein suspension or protein solution is reassociated to a heterogeneous mixture of didecamers or multidecamers by shifting the pH to the range between 6 and 9, preferably between 7 and 8. In a more preferred embodiment, the reassociation is effected by adding $Ca^{++}$ and $Mg^{++}$ ions. More preferably, the amount of $Ca^{++}$ and $Mg^{++}$ ions is lower than 0.5 M, each. More preferred, buffers such as 0.05-0.1 M TRIS/HCl buffer pH 7.4 are employed, optionally together with between 0.05 M and 0.2 M $MgCl_2$, and/or between 0.05 M and 0.2 M $CaCl_2$, and/or between 0.15 M and 0.3 M NaCl. Other buffers are glycine/NaOH pH 7.4, or sodium phosphate, pH 7.4.

Accordingly, the present invention in one embodiment provides a method of producing synthetic KLH or synthetic hemocyanin comprising the steps of dissociating native KLH to obtain subunits, nanofiltering the subunits so-obtained using filters with a pore size between 15 and 35 nm and reassociating the subunits obtained after nanofiltering to obtain the synthetic hemocyanin or synthetic KLH. Preferably the filtration is a cross-flow filtration, more preferably a cross-flow filtration as described above. Typically, the amount of obtained protein is more than 60% per amount of native KLH. More preferably, the obtained (synthetic KLH or synthetic hemocyanin) is more than 70%, more preferably more than 80%, most preferably more than 90% or 93% per amount of native KLH.

The present invention in a third aspect provides the hemolymph obtained by the method of the first and/or second aspect, the hemocyanin or the hemocyanin subunits obtained by the methods of the second aspect of the invention. This aspect includes the provision of immunocyanin, which is a mixture of subunits of a hemocyanin in its naturally occurring ratio.

In a forth aspect, the hemolymph, the hemocyanin or the hemocyanin subunits of the third aspect for use as a medicament are provided.

This aspect also covers a pharmaceutical composition comprising the hemolymph, the hemocyanin or the hemocyanin subunits of the third aspect The pharmaceutical compositions or medicaments are e.g. for use in the treatment of cancer, preferably bladder cancer, or as an immunostimulant or carrier.

According to a fifth aspect hemocyanin subunits are provided, which are the result of a selective dissociation of hemocyanin produced according to the second aspect.

DETAILS OF THE INVENTION

In a first aspect of the invention a method for the preparation of low endotoxin/low bioburden Hemolymph Sera from molluscs such as *Megathura crenulata* in commercial quantities is provided.

In one embodiment, the present invention is directed to the preparation method of a pharmaceutical grade starting material derived from molluscs, preferably keyhole limpets. The low endotoxin/low bioburden quality of Hemolymph Sera is reached by applying a specific quarantine procedure to limpets from natural or aquaculture source. The proprietary design of the Quarantine Aquaria System leads to significant reduction of biological contamination i.e. bacteria, endotoxins and viruses.

One key point of this first aspect of the invention is the treatment of molluscs in a quarantine aquarium system. The animals are kept under specific temperature conditions and/or the quarantine aquaria include means for protein removal such as a centrifugal protein skimmer and/or one or more biofilters.

Preferably, artificial seawater is used in the aquarium and more preferably, a rapid circulation of artificial seawater is employed to treat the molluscs. The current in the aquarium may imitate a surf zone at the sea. Biological contaminants may removed by extensive foaming and/or bio-filtration of the quarantine water.

The Aquarium system of the first aspect leads to the reduction of the biological contaminants. It removes excrements effectively and thereby leads to the removal of bacteria and bacterial endotoxins. During the treatment in the aquarium, the animals are preferably not fed, which again minimized the content of organic ingredients and leads to a reduction of contaminations.

Conductivity, pH-value, and the redox potential of the sea water are preferably controlled and measured permanently.

The water temperature in the natural environment of the keyhole limpets is between 10 and 20° C., preferably between 12-16° C.; therefore cooling of the water in the aquarium is required. For that purpose a heat exchanger may located in the reservoir. The water temperature is monitored by temperature sensors in the basin, controlling cooling units for the set temperature target (14° C.±2° C.).

The water in the aquarium is preferably artificial sea water, i.e. water which is controlled in conductivity and pH, and preferably redox potential and more preferably in addition salt content to resemble sea water. For example, the conductivity value is between 46-52 ms/cm and the pH between 7.5-8.5. In one embodiment, the density may range from 1.020 to 1.030. A redox potential>100 is preferred.

Animals' release for puncturing requires one, preferably two, more preferably three, more preferably four, more preferably five, more preferably six, more preferably seven days, more preferably 10 days, most preferably 13 days of animal holding in the aquarium.

The in-house animal quarantine procedure of the invention aids in reducing the bio-burden. E.g. the animal coliform content can be reduced upon culturing under quarantine conditions.

Upon quarantine, the animals are punctured at their pedal blood sinus under cold narcosis.

A second key point of the first aspect of the present invention, accordingly, is the procedure for puncturing the molluscs. Before the puncture ("hemolymph extraction"), the molluscs are removed from the aquarium, may be examined visually, are preferably washed, and transferred into a clean room facility.

The animals are preferably transferred into a clean room facility, where the animals are rinsed using hemolymph isotonic solution (HIS), a proprietary Sodium Chloride solution whose salt concentration is isotonic with animal sera.

The animals are weighed, and placed on pre set puncture racks.

During this operation preferably care is taken not to cause internal injuries, especially to the intestinal system, for two reasons: first to avoid contamination of the product with fecal matter and secondly to avoid animal death. If accidental injury of the intestinal track arises, as indicated by fecally contaminated hemolymph sera, the material is discarded.

After disinfecting, a puncture may be made in the hind third of the base of the foot with a needle that comprises a lumbal cannula. An inlet of the cannula may be stuck into the foot muscle and may be pushed in further until the pedal sinus is reached. Neither the buccal sinus nor the cardiac sinus is preferably punctured.

In one embodiment, upon completion of the blood extraction, sterile isotonic solution is injected, preferably through the cannula, and liquid leaking out is examined to determine if the blood sinus has been reached, which is indicated by blue fluid.

In a preferred embodiment of the present invention, 10 to 60 ml, more preferably 30-50 ml or 10-20%, preferably 12-15% of the body weight of the animal, of hemolymph is collected in a sterile centrifuge tube.

In one embodiment, the hemolymph that has been withdrawn is replaced by HIS solution.

The hemolymph is preferably refrigerated between 2 and 8° C. and may be pooled.

The animals are preferably transferred back, washed and returned to the in-house recovery aquaria tanks. The animals may be monitored for 1 to 4 days and returned to their natural. This method permits the molluscs to be returned to the ocean alive.

According to a third key point of the first aspect, the obtained blood may be purified and sterilized by 0.2 μm membrane filtration.

Before pooling, the hemolymph fractions must have been shown to correspond to the specifications of the IPC (in process control) performed on the single samples. The cold hemolymph fractions are pooled in a sterile disposable bottle and mixed well, while frothing is avoided.

In a second aspect of the invention a method for the preparation of low endotoxin/low bio-burden hemocyanin or hemocyanin subunits from molluscs such as *Megathura crenulata* in commercial quantities is provided.

Preferably, the method is capable of providing biological safe, virus free molecular standardised hemocyanin, e.g. KLH, or hemocyanin subunits, e.g. KLH subunits in commercial quantities.

The method comprises the isolation of hemocyanin from Hemolymph Sera, preferably via direct chromatography, more preferably via ion exchange chromatography.

The method preferably comprises a step of dissociating hemocyanin into the hemocyanin subunits.

The method may also comprise a step of purifying hemocyanin subunits.

The method preferably also comprises a step of nanofiltration. In this step viruses may be separated from the hemocyanin subunits, i.e. the step is performed in order to remove potential virological contamination.

The method preferably also comprises a step of reassociating the hemocyanin from the subunits.

Hemolymph Sera based on its' origin from a marine mollusc contains apart from hemocyanin and other serum components high levels of Sodium Chloride and other minerals. The conductivity of Hemolymph Sera based on its high salt content is on average around 50 ms/cm. To achieve quantitative binding of hemocanin, e.g. of KLH, the conductivity has to be reduced to <20 mS/cm.

In order to reduce the conductivity as described above the Hemolymph Sera may be partially desalinated by suitable methods such as gel filtration, electrodialysis, diafiltration or dilution. The removal of salts leads to precipitation of the other serum components i.e protein and carbohydrates. The precipitate may be removed by low speed centrifugation, depth filtration or membrane filtration (0.8 u. 0.45 μm).

Subsequently the colloidal dissolved high molecular weight KLH may be isolated by chromatography procedures i.e. ion exchange chromatography, which may then be followed by dissociation and purification of subunits.

Two preferred methods of dissociation of native hemocyanin, such as KLH, are possible: In situ dissociation on an ion exchange capture column or dissociation by Diafiltration.

The obtained hemocyanin subunits may be purified by an additional ion exchange chromatography step and finally polished by gel filtration.

The native, oxygen-binding hemocyanin protein in one embodiment is purified from the hemolymph by Ion Exchange Chromatography. The hemocyanin is be bound to an anion exchanger and then dissociated on the column into the KLH subunits (immunocyanin) in alkaline (pH 7 to 10, preferably 8.6 to 9.6) buffer. The immunocyanin is recovered from the column by means of salt gradient elution. The resulting immunocyanin solution may be desalinated and concentrated by diafiltration/ultrafiltration. The concentrated immunocyanin solution may be subsequently purified by a further ion exchange chromatography step.

In another embodiment, the native, oxygen-binding hemocyanin protein is purified from the hemolymph by Ion Exchange Chromatography. The hemocyanin is bound to an anion exchanger and then recovered from the column by means of salt gradient elution. The resulting hemocyanin solution is desalinated, concentrated and dissociated into the KLH subunits (immunocyanin) by means of diafiltration, dialysis or ultrafiltration in alkaline (pH 7 to 10, preferably 8.6 to 9.6) buffer. Finally the immunocyanin solution may be concentrated followed by a further ion exchange chromatography step.

In another embodiment, the native, oxygen-binding hemocyanin protein is purified from the hemolymph by Ion Exchange Chromatography. The hemocyanin is bound to an anion exchanger and then recovered from the column by means of salt gradient elution. The hemocyanin of the resulting hemocyanin solution is isolated by means of ultracentrifugation. Subsequently the resulting hemocyanin pellets are dissolved and dissociated into the KLH subunits (immunocyanin) in alkaline (pH 7 to 10, preferably 8.6 to 9.6) buffer. Finally the immunocyanin solution may be concentrated followed by a further ion exchange chromatography step.

In order to achieve dissociation of hemocyanin, in general, the hemocyanin may be dissolved in dissociation buffer (pH 8 to 10, preferably 8.6 to 9.6, preferably devoid of $Ca^{++}$ and $Mg^{++}$). This creates alkaline conditions, which lead to dissociation of the native hemocyanin molecule into its subunits.

The immunocyanin solution may be concentrated. Before a final purification (polishing), e.g. by gel filtration, the immunocyanin solution may be concentrated to a protein content of 20 mg/mL (±2.5 mg/mL), e.g. by ultrafiltration. For this purpose, low protein binding polysulfone or polyether sulfone membranes (separation limit: 30,000 Dalton; filter area: ≥700 $cm^2$) mounted in a stainless steel ultrafiltration unit are preferably used. After ultrafiltration, the concentrated immunocyanin solution is filtered, e.g. through a 0.22 μm membrane filter.

The concentrated immunocyanin solution may then purified, e.g. by middle pressure liquid chromatography through a gel filtration column.

A preferred column is Superose® 6 (preparative grade; composed of highly cross-linked porous agarose beads); bead size 20-40 μm, fractionation range 5,000-5,000,000 Da. As eluent an elution buffer (pH 8-10, devoid of $Ca^{++}$ and $Mg^{++}$) may be used. The concentrated immunocyanin solution may be loaded onto the column under aseptic conditions. The main immunocyanin peak at molecular weight 400,000 is collected. The immunocyanin fraction is preferably immediately cooled to +2-8° C. and filtered, e.g. through a 0.22 μm membrane filter.

Due to the origin of native hemocyanins such as KLH a virological risk by human pathogens exist. To guarantee biological safety the downstream process of biologicals preferably contain steps for inactivation or removal of potential virus contamination. The available inactivation methods were tested on KLH and found to be not suitable for hemocyanins because of their damaging effect on the KLH preparations.

According to the present invention nanofiltration is preferably used to obtain purified hemocyanin subunits, e.g. KLH subunits, i.e. for removal of potential virus contamination.

In this step a suitable virus filter membrane, which has no influence on the content and biochemical, chemical and physical characteristics of hemocyanin subunits, e.g. KLH subunits may be selected. Unfiltered and filtered hemocyanin subunits are compared in a comparability study in order to show that the subunits are functionally intact. Virus Validation Study may be performed to show the effect of virus filtration of hemocyanin subunits on the removal of model viruses with different sizes.

In order to demonstrate the safety of pharmaceutical proteins derived from biological sources it is mandatory for the manufacturer of such products to demonstrate the effective inactivation and/or removal of pathogenic viruses during the manufacturing process. Usually, this is done by the deliberate spiking of a down-scaled version of the manufacturing process with relevant and/or model viruses.

According to the present invention, the removal of at least Murine Leukemia Virus, Pseudorabies Virus, Reo Virus Type 3, and Porcine Parvovirus by nanofiltration is performed. In order to test the removal, a test sample will be spiked with the viruses at defined titers and then subjected to nanofiltration. Samples may be withdrawn from the spiked, prefiltered test sample as well as from the nanofiltrate and monitored for virus by endpoint titration and by bulk analysis, respectively.

Removal of viruses is preferably performed in order to reduce the virus titer by 50%, preferably 60%, more preferably 70%, more preferably 80, more preferably 90, more preferably 99%, most preferably 99.9%.

Relevant viruses representing potential contaminants of hemocyanin products are as follows:

therefore provides a severe test for the clearance and reduction capacity of the downstream process system. The human Parvovirus B19 virus can be present at high titres in human plasma, and therefore PPV can be used as a model for B19 in the validation of human plasma derived products. There are also reported incidences of contamination of recombinant products with Parvoviruses such as Murine Minute virus, and PPV can be used as model for this class of virus.

Bovine Viral Diarrhoea Virus (BVDV)

enveloped, medium-sized (~40-60 nm), single-stranded RNA virus (ATCC VR-534) with a medium resistance to physico-chemical inactivation. BVDV belongs to the Flaviviridae family which also contains Hepatitis C and Hepatitis G viruses. BVDV is therefore a suitable model virus where Hepatitis C or G is of concern, particularly in a product derived from human blood, and also for other Flavivirus and Togavirus contaminants, for example where bovine derived material is used.

Simian Virus40 (SV40)

unenveloped, small (~40 nm), double-stranded DNA virus (ATCC VR-305) with high resistance to physico-chemical inactivation. SV40 provides a severe test of the downstream process and its capacity to remove/inactivate viruses. This virus acts as a model for other resistant unenveloped viruses which may be present as contaminants in the starting material, and is a model for papilloma and polyoma virus contaminants.

In the present invention, at least HAV, BVDV, and SV40 are removed, preferably with LRF of more than 2, 3, 4, 5 or 6 for each virus. PPV may be removed with LRF of more than 2, 3 or 4. Alternatively, or in addition, viruses as follows are also removed from the hemocyanin or immunocyanin of the present invention: Murine Leukemia Virus (MuLV), Pseudorabies Virus (PRV) and Reovirus type III (Reo III). These viruses are also removed with LRFs of at least 2 or 3 for each virus.

The stabilisation of virus filtered hemocyanin subunits may be performed by means of lyophilisation. Protein solutions (especially high molecular weight proteins) are in

| Model Virus | Taxonomy | Genome | Structure | Size/nm | Stability | Indicator cell line |
| --- | --- | --- | --- | --- | --- | --- |
| Hepatitis A virus (HAV) | Picornaviridae | ssRNA | non-enveloped | 25-30 | medium to high | FRhK-4 |
| Bovine Viral Diarrhoea Virus (BVDV) | Flavivirus | ssRNA | enveloped | 40-60 | low | MDBK |
| Porcine Parvovirus (PPV) | Parvoviridae | ssDNA | non-enveloped | 18-24 | very high | PK13 |
| Simian Virus 40 (SV40) | Papovaviridae | dsDNA | non-enveloped | 40-50 | high | Vero |

Hepatitis A Virus (HAV)

non-enveloped, small (25-30 nm), single-stranded RNA virus (ATCC VR-1402) with a medium to high resistance to physico-chemical inactivation. Hepatitis A belongs to the Picornaviridae family, which also includes EMCV and Poliovirus. This virus is a potential contaminant of human blood and plasma and therefore should be used where possible in studies. However, the presence of neutralizing antibodies to this virus in blood and plasma products means that its use is limited to situations where this problem does not occur.

Porcine Parvovirus (PPV)

unenveloped, small (~18-25 nm), single-stranded DNA virus (provided by Octapharma AG, Frankfurt, Germany) with a high resistance to physico-chemical inactivation. It general not stable in the long term. During storage protein precipitation together with loss of activity occurs. Storage in stabilising buffer systems or in applicable solutions for pharmaceutical use under refrigerated conditions did not lead to KLH preparations satisfying stability required for pharmaceuticals (2-3 years). Lyophilisation of high molecular weight proteins under retention of their full biological activity is only possible with a suitable mixture of excipients. According to the present invention, protein stabilizers, e.g. lactose, mannitol, sucrose, etc may be used. These stabilizers may be added to the purified immunocyanine solution as solutions with concentrations of 100-700 mg/ml and with a volume of 0.1 ml to 1.0 ml per 1 mg of protein each.

The lyophilised KLH subunits are proofed for their full biological activity and their molecular intactness.

The Stabilisation of virus filtered hemocyanin subunits may also be performed by means of desalination. Desalination by diafiltration with water for injection leads to a salt free highly concentrated (20 mg/ml) hemocyanin subunit solution in water with unexpected long term stability under refrigerated conditions (1-2 years). The salt free hemocyanin subunit solution is the ideal carrier for the manufacturing of conjugated vaccines.

Means and methods for desalination are known by the persons skilled in the art. Typically desalination is performed as long as the conductivity of the filtrate in an iterative filtration process is ≥10 µS/cm or the conductivity of the retentate is ≥150 µS/cm.

The salt free hemocyanin subunits are proofed for their full biological activity and their molecular intactness.

Hemocyanin subunits may be used as a mixture in the ration present in native hemocyanin ("immunocyanin") or single subunits may be separated and used upon isolation.

In order to obtain "synthetic" hemocyanin, the reassociation of the subunits has to be performed, i.e. the refolding of virus filtered KLH subunits.

The size of hemocanin oligomers, e.g. of KLH didecamers (approx. 35 nm), is situated in the same size of large viruses. The described isolation and purification methods (ion exchange chromatography and gel filtration) for native KLH do not lead to the required reduction factors of potential virological contamination according to established guidelines on virological safety of biological products derived from animal sources. Dissociation into the hemocanin subunits reduces the size, in the case of KLH to approx. 400,000 Dalton, and makes the protein accessible to nanofiltration. Refolding is performed with buffer exchange, e.g. by diafiltration or dialysis under reassociation conditions (pH 7-8, $Ca^{++}$, $Mg^{++}$). The reassociated hemocanin may further be purified by gel filtration.

In order to achieve reassociation a reassociation buffer is added to the mixture of hemocyanin subunits.

High molecular weight KLH is manufactured from concentrated immunocyanin solution by buffer exchange to reassociation conditions, pH 7-8, $Ca^{++}$, $Mg^{++}$ and preferably by a concentration step. Both may be achieved by one or more up to a series of ultrafiltration steps using a polysulfone membrane with a nominal separation limit of 50,000 Da.

Further embodiments of the invention are:

1. A method for the preparation of hemolymph sera from a mollusc:
comprising
a) puncturing the pedal blood sinus of the mollusc under cold narcosis.

2. The method of embodiment 1, wherein the mollusc is *Megathura crenulata*.

3. A method of any of embodiment 1 or 2, wherein before puncturing the mollusc is kept under specific quarantine conditions, wherein no organic feed is supplied and/or the water in the aquarium system is purified by removing biological contaminants.

4. The method of any of embodiments 1 to 3, wherein the blood obtained upon puncturing is sterilized by 0.2 µm membrane filtration.

5. The method of isolating native hemocyanin or a mixture of subunits thereof comprising
a) providing hemolymph sera obtained upon performing of any of embodiments 1 to 4,
b) isolating the hemocyanin from hemolymph sera by employing direct chromatography, 6. The method of embodiment 5, wherein the direct chromatography is an ion exchange chromatography.

7. The method of any of embodiments 5 or 6 further including a step of dissociating the hemocyanin into subunits of the hemocyanin oligomer, purifying the KLH subunits and optionally re-associating the subunits into the oligomeric form of the hemocyanin.

8. The method of embodiment 7, wherein the purification is performed employing nanofiltration in order to remove potential biological contamination.

9. The method of any of embodiments 7 or 8, wherein the re-association takes place in a diafiltration step or a gel filtration step.

10. The method of any of embodiments 5 to 9 wherein the hemocyanin is admixed with a stabilizing puffer system for long-term storage.

11. The hemolymph obtained by any of embodiments 1 to 4, the hemocyanin or the mixture of hemocyanin subunits obtained by any of embodiments 5 to 10.

12. The hemolymph obtained by any of embodiments 1 to 4, the hemocyanin or the mixture of hemocyanin subunits obtained by any of embodiments 5 to 10 as a medicament.

14. A pharmaceutical composition comprising the hemolymph obtained by any of embodiments 1 to 4, the hemocyanin or the mixture of hemocyanin subunits obtained by any of embodiments 5 to 10.

15. The hemolymph of embodiment 11 or the hemocyanin of embodiment 12 for use in the treatment of cancer, preferably bladder cancer, or as an immunostimulant or carrier.

16. A method of providing one or more hemocyanin subunits comprising performing the method of any of embodiments 1 to 4 and the method of any of embodiments 5 to 10 and a step of selectively dissociating the so obtained reassociated hemocyanin.

17. The one or more hemocyanin subunits obtained by the method of embodiment 16.

18. The pharmaceutical comprising the one or more hemocyanin subunits of embodiment 17. The one or more hemocyanin subunits of embodiment 17 may be for use in the treatment of cancer or as an immunostimulant.

19. The use of cross-flow filtration for removing viruses from protein formulations.

20. The use of embodiment 19, wherein the protein formulation includes a protein of between 100,000 and 1,000,000 Dalton.

21. The use according to embodiments 19 and 20, wherein the cross-flow filtration employs filters of a pore size between 15 and 35 nm.

EXAMPLES

Example 1: Quarantine of *Megathura Crenulata*

Since the start of the production activities at our facility in Carlsbad, Calif. in February 2002, we have collected 13 batches of animals at various time periods. The collection site ID is the zone number as defined by the Southern California Fisheries Chart (SCFC).

The weather condition in California during the collection of animals for batches MC-001 to MC-013 were not unusual. However, during the more recent batch of animals collected, MC-014, California had experienced unusual rainy conditions prior to animal collection, however, on the day of animal receipt we experienced no rains.

It may be pointed out that the incorporation of test methods has evolved since we started the activities at our facility. The fecal coliform testing on animals, toxic substance, DDT and PCB testing was initiated with lot # MC-002. The pH and Conductivity testing has been done for all lots, the nitrate, nitrite and ammonia testing was initiated on the sea water sample with lot # MC-006.

The pH and conductivity of sea water has a range of 8.0 to 8.3 and 45.0 to 52.4 respectively. The nitrate, nitrite and ammonia content ranged from 0 to 80 ppm, 0 to 0.25 ppm and 0.25 to 1.0 ppm respectively, the high end of the range corresponds to the values for lot MC-014, which, as has been noted was collected post heavy rains. The fecal coliform of sea water samples were <2 MPN/100 mL for samples collected from MC-002 to MC-013 and were 29, 11 and 49 MPN for the most recent lot MC-014 corresponding to the three water samples "0", "50" and "100" respectively.

The DDT and PCB test results indicate that they are below the detection limit of the respective assays. It appears that this may not be an issue in the collection site 718 and 719 where the animals were collected from.

The animal fecal coliform data suggests that the fecal coliform were generally <18 and a maximum of 20 MPN/100 grams for the lot # MC-002 to MC-013, however for MC-014 the values were very high, 3,500 MPN/100 gram. These results in conjunction with the fecal coliform in the surrounding sea water suggest that these animals tend to concentrate the fecal coliform.

On receipt of the laboratory results for fecal coliform in animals, we decided to send samples of animals from our quarantine tanks, 3 animals were taken from Tank Q1 and 3 from Tank Q2, on Jan. 19 2005. The animals were received into our tanks on Jan. 6 2005 and therefore were present in our tank water for 13 days prior to testing. We initiated this testing to determine if the quarantine procedures that we have incorporated into our manufacturing schedule would have an effect on reducing the animal fecal coliform content. The copy of the test report is attached to this report as an attachment. The results indicate that the animal fecal coliform is <18 MPN/100 gram. These results are very encouraging and suggest that the procedures in place are effective in reducing the animal coliform content, if any are present as with this Lot MC-014.

The analysis of the data relating to animals and sea water suggest that:

The pH and conductivity of sea water provide information on the natural sea water conditions and would be useful to compare with our artificial sea water prepared in-house. We currently have a specification for artificial sea water as 7.5 to 8.5 and conductivity 46-52 ms/cm. These specifications seem to match well with the ranges for natural seawater.

The toxicological screening for sea water from collection site was initiated based on advice from Dr. Robert Mooney, Merkel & Associates, used as an external animal health inspector for the first three lots of animal received, namely MC-001 to MC-004. The results to date suggest that DDT and PCB's are not an issue for the area where the limpets are collected from and released into.

The in-house animal quarantine procedure seems to aid in reducing the animal coliform content and is a very useful procedure. Currently, animals release for manufacture require a minimum of seven days from start of quarantine, the animal fecal coliform data for MC-014 was obtained on animals after 13 days of animal holding in our tanks. It may be necessary to initiate a more systematic investigation into the length of quarantine and reduction of fecal coliform and determine if the current set specification of seven days is sufficient. Such studies to be initiated after collection of animals from waters with high coliform as was the case with MC-014.

Example 2: Direct Chromatographic Isolation of Native Hemocyanin from Hemolymph Sera Hemolymph Sera based on its' origin from a marine mollusc contains, apart from hemocyanin and other serum components, high levels of Sodium Chloride and other minerals. The conductivity on average is around 50 ms/cm. Under those present conditions KLH cannot be bound to Ion Exchange resins. To achieve quantitative binding of KLH the conductivity has to be reduced to <20 mS/cm.

In order to reduce the conductivity as described above the Hemolymph Sera is partially desalinated by suitable methods such as gel filtration, electrodialysis, diafiltration or dilution. The removal of salts leads to precipitation of the other serum components i.e protein and carbohydrates. The precipitation is removed by low speed centrifugation, depth filtration or membrane filtration (0.8 u. 0.45 µm).

Subsequently the colloidal dissolved high molecular weight KLH is isolated by chromatography procedures i.e. IEX chromatography followed by dissociation and purification of subunits.

Dissociation of Hemocyanin
Method 1:

The native, oxygen-binding hemocyanin protein is purified from the hemolymph by Ion Exchange Chromatography. The hemocyanin is bound to an anion exchanger and then dissociated on the column into the KLH subunits (immunocyanin) in alkaline (pH 9.6) buffer. The immunocyanin is recovered from the column by means of salt gradient elution. The resulting immunocyanin solution is desalinated and concentrated by diafiltration/ultrafiltration. The concentrated immunocyanin solution may be subsequently purified by a further IEX chromatography step.

Method 2:

The native, oxygen-binding hemocyanin protein is purified from the hemolymph by Ion Exchange Chromatography. The hemocyanin is bound to an anion exchanger and then recovered from the column by means of salt gradient elution. The resulting hemocyanin solution is desalinated, concentrated and dissociated into the KLH subunits (immunocyanin) by means of diafiltration, dialysis or ultrafiltration in alkaline (pH 9.6) buffer. Finally the immunocyanin solution is concentrated followed by purification with a further IEX chromatography step.

The hemocyanin obtained from Method 1/Method 2 is dissolved in dissociation buffer (pH 9.6, devoid of $Ca^{++}$ and $Mg^{++}$). This creates alkaline conditions, which lead to dissociation of the native hemocyanin molecule into its subunits. The entity of these subunits are called immunocyanin.

Method 3:

The native, oxygen-binding hemocyanin protein is purified from the hemolymph by Ion Exchange Chromatography. The hemocyanin is bound to an anion exchanger and then recovered from the column by means of salt gradient elution. The hemocyanin of the resulting hemocyanin solution is isolated by means of ultracentrifugation. The obtained pellets are dissolved in dissociation buffer. Finally, the immunocyanin solution is concentrated and may be purified with a further IEX chromatography step.

Concentration of Immunocyanin Solution

Before final purification (polishing) by gel filtration, the immunocyanin solution is concentrated to a protein content of 20 mg/mL (±2.5 mg/mL) by ultrafiltration. For this purpose, low protein binding polysulfone or polyether sulfone membranes (separation limit: 30,000 Dalton; filter area: ≥700 cm²) mounted in a stainless steel ultrafiltration unit are used.

After ultrafiltration, the concentrated immunocyanin solution is filtered through a 0.22 µm membrane filter.
Purification (Polishing)

The concentrated immunocyanin solution is finally purified by middle pressure liquid chromatography through a gel filtration column.

Example 3: Nanofiltration of Purified KLH Subunits (Immunocyanin)

Due to the origin of native KLH exists a virological risk by human pathogens. To guarantee biological safety the downstream process of biologicals should contain steps for inactivation or removal of potential virus contamination. Commercially available inactivation methods were tested on KLH and found to be not suitable because of their damaging effect on the KLH preparations (pH reduction, heat treatment).

Nanofiltration was previously shown to effectively remove various viruses from protein compositions. However, nanofiltration turned out to not be useful for hemocyanins or native KLH, due to the molecular weight of native KLH from >8 Mill. Dalton. The filters could not discriminate viruses from protein, i.e. the protein is too big to pass the membrane of typical virus filters (pore size between 15 and 35 nm). A reduction to the uniform molecular weight of approx. 400,000 Dalton of KLH subunits was affected. Several virus filters with different pore sizes have been tested in a down scaled process.

Reference Example: Dead End—Filtration Protocol, Virus Filtration of KLH Subunits A protein of approx. 400 KD in a concentration of approx. 5 mg/ml obtained from California see snail's blood has been filtered through Planova 20N, 0.001 m² in Dead-End modus with constant pressure of 2.0 bar. The flow rate was 0.4 ml/min. The protein formulation was at a pH of 9.6 in a glycine/NaOH buffer. 1 g of starting material was applied. With dead-end filtration, 0.1 g of protein in a concentration with 0.5 mg/ml was obtained, i.e. a protein yield of 10%. Also, a reduction of the starting amounts of the protein or the concentration of the protein by a factor of 10 or more did not lead to different results. Also, the reduction of pressure or the increase of size did not lead to changes of protein yield.

Working Example: Cross-Flow Filtration Protocol; Virus Filtration of KLH Subunits A protein of approx. 400 KD in a concentration of approx. 0.45 mg/ml obtained from California sea snails' blood has been filtered through Planova 20N, 0.12 m² in cross-flow modus with a constant pressure of 0.16 bar. Formulation was in a buffer of glycine and NaOH at a pH of 9.6. The amount of starting material was 5,000 g in a concentration of 0.45 mg/ml. The protein amount obtained after nanofiltration was 4,688 g in a concentration of 0.42 mg/ml. This makes up to a yield of 93%.

This example demonstrates that contrary to dead-end filtration, cross-flow filtration enables the filtration of quantitative amounts of hemocyanine protein upon dissociation into its subunits. Nanofilters of a pore size between 15 and 35 nm can be employed which are sufficient to remove the smallest viruses known.

Example 4: Proof of Concept: Feasibility Study

This example demonstrates the suitability of cross-flow filtration for removing small viruses of a diameter of the smallest viruses known. In this example, PPV was tested. PPV has a diameter of 20 nm and the virus was spiked at a concentration of 0.5% per protein. Immunocyanin, a protein of uniform molecular weight of approximately 400,000 Dalton of KLH subunits was spiked with 0.5% PPV. The total virus load in prefiltered was 10,620. The protein amount after virus spiking was 4,814.9 g. Nanofiltration was performed with Planova 20N nanofilters, 0.12 m² in cross-flow mode. The flow-rate chosen was 50 mm/min with a constant pressure of 0.28 bar. 4,662.4 g protein were retained in the filtrate. The LRF for PPV was 3.14+/−0.32. Accordingly, the protein amount was more than 93% with a virus removal of more than 99.9%.

This example shows that cross-flow filtration is suitable for the preparation of KLH or KLH subunits in a virus free form on a commercially relevant scale with a yield of more than 90%.

Example 5: Stabilisation of Purified KLH Subunits by Means of Desalination

Das Folgende würde ich noch kürzer zusammenfassen, so z.B.!
Principle

KLH BULK LIQUID salt-free is manufactured from purified immunocyanin by desalination and concentration. Both are achieved by a series of ultrafiltration steps using a polysulfone membrane with a nominal separation limit of 30,000 Da.
Preparation of the Desalination Batch In order to minimize batch-to-batch variations during the desalination process, purified immunocyanin solution is concentrated to an immunocyanin content of between 10 mg/ml and 40 mg/ml (±2 mg/ml) by ultrafiltration. For this purpose, low protein binding polysulfone or polyether sulfone membranes (separation limit: 30,000 Da) mounted in a stainless steel ultrafiltration unit are used. Before use, the membranes are conditioned by recirculation with alkaline dissociation buffer at a temperature of +2-8° C. Flow is achieved by a peristaltic pump. Finally, the conditioning is tested by in-process control pH and bacterial endotoxins. Before starting the concentration process, the ultrafiltration unit is checked for integrity.
Concentration The immunocyanin solution is now transferred to the ultrafiltration unit and recirculated at +2-8° C. The concentration is controlled be weighing the obtained ultrafiltrate. The maximal entrance pressure of the ultrafiltration unit should not exceed 1 bar, preferably not 0.5 bar. The immunocyanin solution is recirculated until the calculated amount of ultrafiltrate has been collected. Finally, the concentrate is tested by in-process control pH value, osmolality, conductivity, immunocyanin content.
Desalination The concentrated immunocyanin solution (=concentrated desalination batch) is either desalinated by dilution 1+1 with water for injections at each ultrafiltration cycle or alternatively by adding the water for injections employing constant volume wash procedure. The desalination process is controlled by weighing the ultrafiltrate, the concentrated desalination batch and testing of conductivity of the ultrafiltrate and the desalination batch.

If the conductivity of the ultrafiltrate has reached <10 µS/cm or if the conductivity of the concentrated desalination batch is <150 µS/cm, the desalination process is terminated and the immunocyanin content of the desalination batch is determined in order to prepare the final batch of KLH BULK LIQUID salt-free.

Preparation of the Final Batch of KLH BULK LIQUID Salt-Free

The final batch of KLH BULK LIQUID salt-free is prepared from the immunocyanin concentrate by dilution to an immunocyanin content of 20 mg/ml. For this purpose, the filtered immunocyanin concentrate is weighed. The required amount of water for injections is weighed accurately and slowly added to the filtered immunocyanin concentrate. The solution is gently mixed, and a sample for in-process control is removed pH value, density, osmolality, conductivity, immunocyanin content.

The released solution is finally sterilized by filtration through a 0.22 µm membrane filter directly into infusion bags.

They are stored at +2-8° C.

During filtration, samples for quality control are removed.

Example 6: Refolding of Virus Filtered KLH Subunits and Final Purification

Principle

High molecular weight KLH is manufactured from concentrated immunocyanin solution by diafiltration (buffer exchange to reassociation conditions, pH 7-8, $Ca^{++}$, $Mg^{++}$) and concentration. Both are, e.g. achieved by a series of ultrafiltration steps using a polysulfone membrane with a nominal separation limit of 50,000 Da.

Concentration of the Purified Immunocyanin Solution

In order to optimize reassociation conditions, purified immunocyanin solution is concentrated to an immunocyanin content of 20 mg/mL (±2 mg/mL) by ultrafiltration. For this purpose, low protein binding polysulfone or polyether sulfone membranes (separation limit: 30,000 Da) mounted in a stainless steel ultrafiltration unit are used. Before use, the membranes are conditioned with elution buffer as follows. The ultrafiltration system is first rinsed with elution buffer at a temperature of +2-8° C., while the filtrate outlets are closed. Flow is achieved by a peristaltic pump. Finally, the elution buffer is completely removed from the system. A sample is removed from the retentate side for in-process control pH, bacterial endotoxins. Before starting the concentration process, the ultrafiltration unit is checked for integrity.

The immunocyanin solution is now transferred to the retentate bag of the ultrafiltration unit. The recirculation is started, and the ultrafiltrate is collected in a weighed beaker. The temperature is kept at +2-8° C. As during conditioning, the maximal entrance pressure of the ultrafiltration unit should not exceed 1 bar. The immunocyanin solution is recirculated until the calculated amount of ultrafiltrate has been collected. The retentate is mixed, while the filtrate outlets are closed, and a sample is removed for in-process control pH value, osmolality, conductivity, immunocyanin content.

Reassociation

In order to refold the KLH subunits a second ultrafiltration system with low protein binding polysulfone or polyether sulfone membranes (separation limit: 50,000 Da) mounted in a stainless steel ultrafiltration unit are used. Before use, the membranes are conditioned with reassociation buffer as follows. The ultrafiltration system is first rinsed with reassociation buffer at a temperature of +2-8° C., while the filtrate outlets are closed. Flow is achieved by a peristaltic pump. Finally, the reassociation buffer is completely removed from the system. A sample is removed from the retentate side for in-process control pH, bacterial endotoxins. Before starting the reassociation process, the ultrafiltration unit is checked for integrity.

For reassociation the ultrafiltration system is recirculated with reassociation buffer (between 2- to 10-fold volume of concentrated immunocyanin solution) while the filtrate outlets are closed. The concentrated immunocyanin solution is slowly injected in the recirculated reassociation buffer. The temperature during the whole reassociation process is kept at a temperature of +2-8° C. After complete injection of the concentrated immunocyanin solution the reassociation batch is diafiltrated against between 2- and 10-fold of reassociation buffer applying the constant volume wash procedure. Finally the batch is concentrated to a KLH content of 20 mg/ml. After reassociation, the concentrated KLH solution, is filtered through a 0.22 µm membrane filter.

Purification of Refolded KLH by Gel Filtration

The concentrated KLH solution is finally purified by middle pressure liquid chromatography through a gel filtration column.

Biological Activity and Potency—Comparability with Native KLH

Native KLH and synthetic KLH obtained after reassociating according to the method of the present invention were compared. Synthetic KLH and native KLH were compared via CD-spectroscopy. Bands in CD-spectroscopy were identical.

The protein bands in SDS PAGE were identical when comparing synthetic and native KLH. In synthetic KLH, no protein fragments are found.

2-dimensional immunoelectrophoresis was also performed to compare synthetic and native KLH. Anti-KLH1 and anti-KLH sera were used. The immunoelectrophoretic patterns were identical for both, native and synthetic, KLH. Two precipitation maxima (one for KLH1 and one for KLH2) occur for both native and synthetic KLH.

Electromicroscopic investigations both, native and synthetic, KLH show the typical decamers, didecamers, and tridecamers.

Native PAGE and densiometric tests show that both synthetic and native KLH include the typical protein bands. A ratio between KLH1 and KLH2 between 0.9 and 1.0 for both, synthetic and native, KLH was obtained.

Example 9: Anion—Exchange Chromatography

For the isolation, purification and in situ dissociation of hemocyanin anion exchange chromatography was selected because of its isoelectric point (pI) at ~pH 6 and the negative charge at pH>7.

Hydrophobic interaction separation was involved because of applying different conditions of those used in ion exchange chromatography (IEX). In this separation, a buffer with a high ionic strength, usually ammonium sulfate, is initially applied to the column. The salt in the buffer reduces the solvation of sample solutes thus as solvation decreases, hydrophobic regions that become exposed are adsorbed by the medium.

In a first series of binding studies using hemocyanin solutions with low salt concentration different strong and weak anion exchange media packed in columns (bed volumes approx. 20-50 ml) as well as different HIC columns were proofed on their binding capacity.

Strong and weak anion exchange media were selected due to their specific binding properties and selectivity:

Poros® 50 micron media for perfusion chromatography (HQ—strong anion exchanger, functional group: quaternized polyethyleneimine; PI—weak anion exchanger, functional group: quaternized polyethyleneimine; D—weak anion exchanger, functional group: dimethyl amino alkyl groups DEAE).

The Poros® 50 micron media were used because of their robust chemical stability, particle size of 50 μm, and the large pore structure (appr. 6000 Å) which enables high flow rates without compromising capacity or resolution.

Q-Sepharose FF and HP (strong anion exchanger) with particle sizes of 90 μm and 34 μm were also tested alternatively. The functional groups exists of quarternary ammonium. Hydrophobic interaction chromatography tests were performed using a HiTrap HIC Selection Kit, which contains prepacked columns ready to use (HiTrap HIC Phenyl FF high sub 1 ml, HiTrap HIC Phenyl FF low sub 1 ml, HiTrap HIC Butyl FF 1 ml and HiTrap HIC Octyl FF 1 ml).

In summary no or only minor binding of hemocyanin could be obtained with the hydrophobic interaction chromatography media. The Q-Sepharose FF and HP and the weak anion exchanger of the Poros® media (PI and D) showed only less to medium binding. The highest binding capacity of approx. 20 mg KLH per ml gel has been proofed with Poros® 50 micron HQ media.

Based on the obtained results the developmental work was continued in order to purify KLH directly from the starting material Hemolymph Sera.

Hemolymph Sera based on its origin from a marine mollusc contains apart from hemocyanin and other serum components high levels of sodium chloride and other minerals. The conductivity on average is around 50 mS/cm. Under those present conditions KLH could not be bound to the selected Poros® 50 HQ media.

In order to achieve quantitative binding of KLH the hemolymph sera was diluted with TRIS/HCl buffer (pH 7.4, including $CaCl_2$, $MgCl_2$ and NaCl), so called IEXdilution buffer. The precipitation occurred during dilution was removed by prefiltration steps.

4 (four) dilution series were tested to determine the binding capacity of Poros® 50 HQ media for KLH (hemolymph sera diluted to approx. 25 mS/cm, 20 mS/cm, 15 mS/cm and 10 mS/cm). Tests were performed on Poros® 50 HQ columns (approx. 50 ml gel). The elution of KLH started at approx. 27 mS/cm.

Flow rate sample: 5 ml/min
Flow rate elution: 10 ml/min
Elution gradient: 0.15 to 0.65 M sodium chloride, TRIS/HCl buffer (pH 7.4, including CaCl2, MgCl2 and NaCl).

The binding studies showed that the hemolymph sera has to be diluted to <20 mS/cm to achieve quantitative binding of KLH.

Subsequently additional test runs with hemolymph sera diluted to approx. 19 mS/cm were performed to optimize KLH binding addicted to the sample feeding velocity. 4 (four) different sample flows (4.0 ml/min, 4.6 ml/min, 5.2 ml/min and 8.0 ml/min) were tested under the conditions described above. The obtained results demonstrated the correlation between feeding velocity and binding capacity of the anion exchanger media. With the lowest flow rate of 4.0 ml/min (corresponding to a linear flow rate of approx. 50 cm/h) approx. 23 mg KLH per ml gel were bound and even with the highest flow rate of 8.0 ml/min (corresponding to a linear flow rate of approx. 100 cm/h) the achieved binding of approx. 17 mg KLH per ml gel was excellent. Break through of KLH was monitored by UV detection at 280 and 340 nm. Subsequently further trials were initiated in lab scale as well as during scale up to optimize the chromatography parameter due to an effective and economic isolation and purification process.

In addition in situ dissociation was tested on KLH captured on the Poros® 50 HQ column applying the chromatography parameters as described above. After a first rinsing step with TRIS/HCl buffer (pH 7.4, including $CaCl_2$, $MgCl_2$ and NaCl) buffer exchange with glycine/NaOH buffer (pH 9.6, including NaCl, EDTA) was performed. No breakthrough of KLH was observed during rinsing the column under dissociation conditions.

Elution of the KLH subunit fraction was achieved using a elution gradient of 0.075 to 0.575 M sodium chloride, glycine/NaOH buffer (pH 9.6, including NaCl, EDTA).

The degree of dissociation was determined by means of analytical MPLC/SEC (FPLC®; separating column: Superose® 6 HR 10/30, molecular weight separation range $5 \times 10^3$-$5 \times 10^6$ Da) and by means of native PAGE. The measurement of the subunit fraction showed that an almost quantitative dissociation into the KLH subunits was achieved on the column. Due to the concentration of KLH subunits (approx. 20 mg/ml) the filtered fraction (0.22 μm membrane filter) was used for further purification by gel filtration without any additional processing.

At the end of the research program, anion exchange chromatography was the method of choice.

The invention claimed is:

1. A method of isolating and/or purifying hemocyanin or immunocyanin comprising the steps of:
   a) providing a hemocyanin formulation, wherein the hemocyanin formulation is a hemolymph serum derived from a marine mollusk;
   b) reducing the conductivity of the formulation provided in step a) to a value of between 30 mS/cm and 10 mS/cm by adding a dilution buffer to the formulation provided in step a);
   c) adding the diluted hemocyanin formulation obtained in step b) to an anion exchange chromatography column, wherein the diluted hemocyanin formulation is a diluted hemolymph serum, and wherein the diluted hemolymph serum contains serum proteins other than KLH;
   d) rinsing the column with a second buffer; and
   e) eluting the hemocyanin or immunocyanin from the column by adding a third buffer.

2. The method of claim 1, wherein the matrix material is an anion exchange matrix including particles of a particle size of more than 30 μm, preferably 50 μm +/− 5 μm.

3. The method of claim 1, wherein the anion exchange matrix includes pores of a pore size between 3,000 and 8,000 Angstroms.

4. The method of claim 1, wherein the rinsing in step (d) removes salts, carbohydrates and proteins other than KLH.

5. The method according to claim 1 wherein the second buffer has a pH between 7 and 8.

6. The method of claim 5, wherein the anion exchange matrix includes pores of a pore size between 3,000 and 8,000 Angstroms.

7. The method of claim 5, wherein hemocyanin is eluted, wherein the third buffer has a pH between 7 and 8 and comprises $Ca^{++}$ and $Mg^{++}$ ions.

8. The method of claim 7, wherein the matrix material is an anion exchange matrix including particles of a particle size of more than 30 μm, preferably 50 μm+/−5 μm.

9. The method of claim 8, wherein the anion exchange matrix includes pores of a pore size between 3,000 and 8,000 Angstroms.

10. The method of claim 5, wherein immunocyanin is eluted, wherein the third buffer has a pH between 9 and 10 and is free from $Ca^{++}$ and $Mg^{++}$ ions.

11. The method of claim 10, wherein the matrix material is an anion exchange matrix including particles of a particle size of more than 30 μm, preferably 50 μm+/−5 μm.

12. The method of claim 11, wherein the anion exchange matrix includes pores of a pore size between 3,000 and 8,000 Angstroms.

13. The method of claim 1, wherein hemocyanin is eluted, wherein the third buffer has a pH between 7 and 8 and comprises $Ca^{++}$ and $Mg^{++}$ ions.

14. The method of claim 13, wherein the matrix material is an anion exchange matrix including particles of a particle size of more than 30 μm, preferably 50 μm+/−5 μm.

15. The method of claim 13, wherein the anion exchange matrix includes pores of a pore size between 3,000 and 8,000 Angstroms.

16. The method of claim 1, wherein immunocyanin is eluted, wherein the third buffer has a pH between 9 and 10 and is free from $Ca^{++}$ and $Mg^{++}$ ions.

17. The method of claim 16, wherein the matrix material is an anion exchange matrix including particles of a particle size of more than 30 μm, preferably 50 μm+/−5 μm.

18. The method of claim 16, wherein the anion exchange matrix includes pores of a pore size between 3,000 and 8,000 Angstroms.

\* \* \* \* \*